United States Patent [19]

Zelonka

[11] 4,341,907
[45] Jul. 27, 1982

[54] CATALYTIC OXIDATION OF CYCLOPARAFFINS

[75] Inventor: Ronald A. Zelonka, Whitby, Canada

[73] Assignee: Du Pont Canada Inc., Mississauga, Canada

[21] Appl. No.: 229,873

[22] Filed: Jan. 30, 1981

Related U.S. Application Data

[63] Continuation-in-part of Ser. No. 74,096, Sep. 10, 1979, abandoned.

[30] Foreign Application Priority Data

Sep. 19, 1978 [GB] United Kingdom ............... 37305/78

[51] Int. Cl.³ .................... C07C 45/00; C07C 7/12
[52] U.S. Cl. .................................. 568/360; 568/376; 568/573; 568/570; 568/575; 568/821; 568/836
[58] Field of Search ............... 568/360, 376, 573, 570, 568/575, 821, 836

[56] References Cited

U.S. PATENT DOCUMENTS

| 2,734,086 | 2/1956 | Goppel et al. | 568/573 |
| 3,404,185 | 10/1968 | Thomas et al. | 260/586 P |
| 3,723,542 | 3/1973 | Risco et al. | 568/570 |
| 3,855,307 | 12/1974 | Rony et al. | 568/836 |
| 3,917,708 | 11/1975 | Kuessner et al. | 568/836 |

*Primary Examiner*—John F. Niebling

[57] ABSTRACT

A process is disclosed for the catalytic oxidation of a cycloparaffin, e.g., cyclohexane, to partial oxidation products thereof, especially for the production of mixtures of cycloalkanols and cycloalkanones. In the process, molecular oxygen, usually in the presence of an inert gas, is introduced into the cycloparaffin at elevated pressure and a temperature of 130°–180° C., in the presence of an oxidation catalyst comprising a heavy metal compound along with an N-heterocyclic compound. The heavy metal of the heavy metal compound may be cobalt, vanadium, manganese, copper, iron or nickel. The heavy metal compound may have ligands of alkanoate, dialkylphosphate, dicycloalkylphosphate or alkylcycloalkylphosphate. The N-heterocyclic compound may be dipyridyl, pyrimidine, pyrazine, pyridine and pyridine substituted with —CN, —R, and/or —OR where R is alkyl. A preferred catalyst is cobalt bis[di(2-ethylhexyl)phosphate] in combination with pyridine.

4 Claims, No Drawings

CATALYTIC OXIDATION OF CYCLOPARAFFINS

CROSS REFERENCE TO RELATED APPLICATION

This application is a continuation-in-part of my prior copending U.S. application, Ser. No. 074,096, filed Sept. 10, 1979, now abandoned.

BACKGROUND

1. Field of the Invention

The present invention relates to a process for the catalytic oxidation of liquid cycloparaffins and, in particular, to an improvement in the catalytic oxidation of liquid cycloparaffins, especially cyclohexane, in which the oxidation catalyst is a heavy metal compound in combination with an N-heterocyclic compound.

2. Description of the Prior Art

The oxidation of cycloparaffins to produce useful partial oxidation products, for example, the oxidation of cyclohexane to cyclohexanol and cyclohexanone, is known as one important step in the manufacture of nylon intermediates, for example, adipic acid. In the case of adipic acid manufacture, it has been found to be preferable to oxidize cyclohexane to adipic acid in a two-step oxidation process, i.e., to oxidize cyclohexane to a mixture of cyclohexanol and cyclohexanone and to thereafter oxidize that mixture to adipic acid by means of a nitric acid oxidation process.

A process in which cyclohexane is oxidized in the liquid phase to cyclohexanol and cyclohexanone at low conversion and high yields was disclosed by Donald J. Loder in Canadian Pat. No. 401,788, which issued Dec. 30, 1941. In the Loder process, the preferred catalysts include cobalt alkanoate, especially cobalt naphthenate. The yields of cyclohexanol and cyclohexanone obtained by the Loder process were considerably higher than had been achieved in earlier processes not employing catalysts or initiators. While Loder's process when operated on a noncommercial scale can be made to give yields of cyclohexanol plus cyclohexanone from cyclohexane of 85-95%, in practical commercial operations it is often necessary to compromise on yield in favor of other process parameters in order to have a continuous process which can be run in an economical manner.

It is known that the quantities of useful oxidation products and the by-products of the oxidation of cycloparaffins depend on, in particular, the temperature, residence time, oxygen concentration and flow rates of cycloparaffin, and the like. An improvement in the method for the oxidation of cyclohexane and for the control of the oxidation products so obtained is discussed by K. Pugi in Canadian Pat. No. 745,204, which issued Oct. 25, 1966.

A process for the catalytic oxidation of cycloparaffins to the corresponding cycloalkanol and cycloalkanone in the presence of a catalyst that is, for example, a cobalt monoalkylphosphate and/or cobalt dialkylphosphate, is disclosed by A. Kuessner et al. in U.S. Pat. No. 3,917,708, which issued Nov. 4, 1975.

Commercial processes for the oxidation of liquid cycloparaffins are usually operated on such a large scale that there are significant incentives to increase the efficiency of the process, especially with respect to the unit cost, e.g., the cost per ton of product, for the manufacture of useful oxidation products. The percentage yield of useful products, per mole of cycloparaffin oxidized, and the amount of cycloparaffin oxidized, i.e., the conversion, obtained as a result of one pass of cycloparaffin through the oxidation zone of the process, are both important process parameters. Such parameters have a major effect on the productivity of the process, i.e., the amount of useful oxidized products formed in the process in a given period of time, which is a prime factor in determining the unit cost for the manufacture of useful oxidation products.

It has now been found that cycloparaffins may be catalytically oxidized to useful partial oxidation products by using a process in which the oxidation catalyst is a heavy metal compound in combination with an N-heterocyclic compound.

SUMMARY OF THE INVENTION

Accordingly, the present invention provides a process for the catalytic oxidation of a liquid cycloparaffin to partial oxidation products thereof, which comprises introducing a molecular oxygen-containing gas into a cycloparaffin of from 5 to 12 carbon atoms at elevated pressure and a temperature of from 130° to 180° C. and in the presence of an oxidation catalyst comprising a heavy metal compound along with an N-heterocyclic compound, said oxidation catalyst being soluble in the cycloparaffin, the heavy metal of the heavy metal compound being selected from the group consisting of cobalt, vanadium, manganese, copper, iron and nickel, and mixtures thereof, and said heavy metal compound having ligands selected from the group consisting of alkanoate, dialkyl phosphate, dicycloalkylphosphate and alkylcycloalkylphosphate, and mixtures thereof, said alkanoate and said alkyl group having from 6 to 18 carbon atoms, with the proviso that the alkyl group of the dialkylphosphate is a branched alkyl group and said cycloalkyl group having 5 to 12 carbon atoms, said N-heterocyclic compound being selected from the group consisting of dipyridyl, pyrimidine, pyrazine, pyridine and pyridine substituted with —CN, —R, and- /or —OR, where R is an alkyl group of 1 to 8 carbon atoms.

In a preferred embodiment of the process of the present invention, the cycloparaffin is cyclohexane or cyclododecane.

In another embodiment, the ligand is dialkyl phosphate in which the alkyl group is branched in the $\beta$ position.

In a further embodiment, the heavy metal compound of the catalyst is cobalt bis(dialkylphosphate).

In yet another embodiment, the N-heterocyclic compound is pyridine.

DETAILED DESCRIPTION OF THE INVENTION

As mentioned above, the present invention relates to the catalytic oxidation of cycloparaffins to form partial oxidation products, especially cycloalkanols and cycloalkanones. The cycloparaffins that may be oxidized according to the invention have from 5 to 12 carbon atoms and are, for example, cyclopentane, cyclohexane, cyclooctane and cyclododecane. The preferred cycloparaffin is cyclohexane, the cycloparaffin of greatest industrial importance. The present invention generally is described hereafter with reference to cyclohexane as the cycloparaffin.

Oxidation is effected by contacting cyclohexane with molecular oxygen in the presence of an oxidation catalyst and at a temperature in the range of 130° to 180° C.

The preferred operating temperature will depend in particular on whether it is desired to operate the process at relatively low or relatively high levels of productivity, typically relatively low or relatively high levels of conversion of cyclohexane, respectively, of useful oxidation products. The former tend to be operated in a temperature range of about 130° to about 160° C., while the latter tend to be operated in a temperature range of about 160° to about 180° C. Both types of processes are known commercially. In the process of K. Pugi, referred to hereinbefore, liquid cyclohexane is contacted at elevated pressure and normally at a temperature of about 160° to about 180° C., at each of several immediately successive stages of an oxidation zone with a mixture of gases comprising molecular oxygen, at controlled partial pressure, and inert gas. The mixture of gases passes countercurrent to the cyclohexane. The oxidation is usually carried out in the presence of an oxidation catalyst. A stream of cyclohexane containing oxidation products of cyclohexane is recovered from the last of the immediately successive stages.

The pressure at which the process is operated may be varied over a wide range, the actual pressure being governed primarily by other process parameters. Typical operating pressures are in the range 500 to 2500 kPa.

As stated above, oxidation is effected by contacting cyclohexane with molecular oxygen in the presence of an oxidation catalyst. The molecular oxygen is preferably introduced in the form of air. The molecular oxygen may, however, be admixed with nitrogen in proportions other than that of air or with other inert gases. Such other inert gases may be any gas or vapor which cannot itself react with cyclohexane or be substantially oxidized under the conditions of the oxidation reaction. Consideration must, however, be given at all times to operating the process of the present invention such that gaseous mixtures formed in the process are not in the explosive range.

The oxidation catalyst of the present invention is a heavy metal compound in combination with an N-heterocyclic compound. The heavy metal of the heavy metal compound may be cobalt, vanadium, manganese, copper, iron and/or nickel. The preferred metal is cobalt. The ligand of the heavy metal compound may be alkanoate, dialkylphosphate, dicyclohexylphosphate or alkylcycloalkylphosphate, and mixtures thereof, such mixtures including, for example, mixtures of alkanoate ligands. Dialkylphosphate ligands are preferred. The alkanoate ligand and the alkyl group of the phosphate ligand of the heavy metal compound has 6 to 18 carbon atoms. Preferably, the alkanoate group is ethylhexanoate or that known as naphthenate. The alkyl group of the dialkylphosphate ligand is a branched alkyl group, preferably an alkyl group branched at the $\beta$ position. The cycloalkyl group may have 5 to 12 carbon atoms. The preferred dialkylphosphate ligand is di(2-ethylhexyl) phosphate. The preferred heavy metal compound is cobalt bis[di(2-ethylhexyl)phosphate].

As stated hereinbefore, the heavy metal compound is in combination with an N-heterocyclic compound. The N-heterocyclic compound may be dipyridyl, pyrimidine, pyrazine or pyridine. The pyridine may be substituted with a —CN, —R, and/or —OR group, where R is an alkyl group of 1 to 8 carbon atoms. The preferred N-heterocyclic compound is pyridine.

In a preferred embodiment of the present invention, the oxidation catalyst is cobalt bis[di(2-ethylhexyl)phosphate] in combination with pyridine.

The oxidation catalyst is preferably prepared, usually in the cycloparaffin to be oxidized, by premixing the components or by admixing the components immediately prior to feeding the resultant catalyst to the oxidation zone. It is preferred that the mixing occurs before the oxidation catalyst is fed to the oxidation zone in order to facilitate the interaction, and any resultant "complex" formation that is believed to occur in solution between such compounds. Admixing after entering the oxidation zone tends to be less effective because of dilution effects. The relative amounts of heavy metal compound and N-heterocyclic compound may be varied over a wide range, for example, using molar ratios of N-heterocyclic compound to heavy metal compound of from 1:1 to 20:1. A particularly suitable ratio is a molar ratio of N-heterocyclic compound: heavy metal compound of 4:1.

The oxidation catalyst fed to the oxidation zone must be soluble in the cycloparaffin, e.g., cyclohexane, at the temperature of the cycloparaffin in the zone. For practical reasons, the oxidation catalyst is usually formed at temperatures below the temperature of the oxidation zone, especially at temperatures near 25° C. Thus, the oxidation catalyst is preferably soluble in the cycloparaffin at temperatures of from about 25° C. to at least that of the oxidation zone.

The concentration of catalyst may be varied over a wide range, for example, from 0.1 to 10 ppm of heavy metal in the catalyst fed to the oxidation zone. As will be appreciated by those skilled in the art, the catalyst is normally initially formed at temperatures well below that of the oxidation zone as a concentrate in hydrocarbon, for example, with a heavy metal concentration of at least 0.1%, especially at least 1%, and then admixed with the hydrocarbon being oxidized. Catalysts capable of being formed into such concentrates are regarded as catalysts that are soluble in the hydrocarbon being oxidized.

The oxidation products of the process of the present invention are normally subjected to further processing steps, e.g., so as to obtain adipic acid if the cycloparaffin is cyclohexane, as is known in the art. One such further processing step may be a preparatory treatment step, prior to further oxidation to adipic acid, known as a "wet KA" process, which was disclosed by M. Goldbeck, Jr. et al. in Canadian Pat. No. 546,287, which issued Sept. 17, 1957. In that process, an oil distillate is first obtained by injecting water into the partial oxidation products leaving the oxidation zone. Hydrocarbon and aqueous phases are then separated from the resulting mixtures and steam-distillable oil is removed from the aqueous phase. The oil is added to the hydrocarbon phase whereupon substantially all of the hydrocarbon is stripped therefrom and the residue steam-distilled to provide a suitable feed for a nitric acid oxidation process. The presence of water is advantageous during the recovery of cyclohexane from the partial oxidation products because it suppresses dehydration of cyclohexanol and cyclohexanone to such products as cyclohexylidene cyclohexanone, cyclohexyl ethers and cyclohexyl esters.

The present invention is illustrated by the following examples.

EXAMPLE I

Cyclohexane was fed on a continuous basis to a stirred one-liter reactor. The volume of liquid in the reactor was controlled at approximately 450 ml. In the reactor, the cyclohexane was maintained at a temperature of 170° C. and under a pressure of 1190 kPa. Molecular oxygen in the form of air was fed to the reactor at a rate of 181 liters at 21° C. and atmospheric pressure per hour. Oxidation catalyst in cyclohexane solution was also fed to the reactor on a continuous basis.

The streams containing cyclohexane and its partial oxidation products that passed from the reactor were collected for a period of one hour and then analyzed using gas chromatographic and coulometric techniques. Gaseous products were also analyzed.

Further process details and the results obtained are given in Table I.

The results given in Table I and in the Examples II–IV hereinafter, are average results for three consecutive one-hour tared runs.

The results given in Table I show that at a constant cyclohexane feed rate, residence time and catalyst concentration, as measured by the concentration of cobalt in the catalyst fed to the reactor, the process of the present invention showed an increased cyclohexane conversion, increased yield of partial oxidation products, as measured by the combined yield of cyclohexanol (A), cyclohexanone (K) and cyclohexylhydroperoxide (P, also known as CHHP), viz., K+A+P or KAP, and in particular, an increased productivity or rate of production of KAP.

EXAMPLE II

The procedure of Example I was repeated using catalyst CA, i.e., a catalyst of the process of the invention, and catalyst CD, a known catalyst not of the process of the invention, at different catalyst concentrations, catalysts CA and CD being defined in Table I.

Further process details are the results obtained are given in Table II.

The results show the superior performance of the process of the present invention, especially as measured by productivity.

EXAMPLE III

Using the procedure of Example I, runs were carried out at a reduced residence time. Process details and the results obtained are given in Table III.

The results shown again the superior performance of a process of the invention.

EXAMPLE IV

The procedure of Example I was repeated using three catalysts of the process of the invention and catalyst CD for comparison. Further details and the results obtained are given in Table IV.

The results further illustrate the productivity obtainable using a process of the invention.

EXAMPLE V

A number of cobalt compounds were formed in situ in cyclohexane by admixing solutions in cyclohexane, of cobalt di(2-ethylhexanoate) and a phosphate ester. The solubility of the cobalt compounds was noted. An N-heterocyclic compound dissolved in cyclohexane was then added to the cobalt compound and the solubility of the resultant combination was noted. Further details and the results obtained are given in Table V.

It will be noted that only some of the combinations of cobalt compounds and N-heterocyclic compounds are soluble in cyclohexane.

EXAMPLE VI

Cyclohexane was fed to the top of a vertical column reactor of a commercial-scale cyclohexane oxidation process. Oxidation catalyst in cyclohexane solution was fed to the column reactor on a continuous basis. A molecular oxygen-containing gas in the form of air was also fed to the column reactor. The temperature of the cyclohexane in the reactor varied over a range of from about 160° to about 175° C. in different parts of the column.

The streams containing cyclohexane and its partial oxidation products that passed from the bottom of the column reactor were sampled and analyzed using gas chromatographic and coulometric techniques. Gaseous products were also analyzed.

Further process details and the results obtained are given in Table VI.

TABLE I

| Run No. | 1 | 2** | 3** | 4** | 5** | 6** |
|---|---|---|---|---|---|---|
| Catalyst* | CA | CB | CC | CD | CE | — |
| Catalyst Concentration in Reactor Feed (ppm of cobalt) | 1.4 | 1.4 | 1.4 | 1.4 | 1.4 | 0 |
| Cyclohexane Feed Rate (g/hr) | 2490 | 2490 | 2510 | 2500 | 2495 | 2520 |
| Residence Time in Reactor (min) | 8.5 | 8.5 | 8.5 | 8.5 | 8.5 | 8.5 |
| Cyclohexane Conversion (%) | 4.12 | 3.99 | 3.97 | 3.94 | 3.95 | 3.69 |
| Yield (%) | | | | | | |
| K | 20.9 | 16.8 | 18.4 | 23.9 | 23.0 | 16.9 |
| A | 35.6 | 29.3 | 33.8 | 38.5 | 35.5 | 28.7 |
| P | 15.1 | 21.5 | 18.2 | 7.8 | 10.8 | 21.2 |
| Total (K + A + P) | 71.6 | 67.6 | 70.4 | 70.2 | 69.3 | 66.9 |
| Productivity of KAP (g/hr) | 89.9 | 83.8 | 86.6 | 83.3 | 82.8 | 77.8 |

*CA = cobalt bis[di(2-ethylhexyl)phosphate] in combination with pyridine at a molar ratio of pyridine:cobalt of 4:1
CB = cobalt bis[di(isoamyl)phosphate]
CC = cobalt bis[di(2-ethylhexyl)phosphate]
CD = cobalt bis(2-ethylhexanoate)
CE = cobalt adipate
**Runs 2–5 are comparative runs. The oxidation catalyst does not contain an N-heterocyclic compound. Run 6 is a comparative run in which the oxidation was uncatalyzed.

TABLE II

| Run No. | 7* | 8 | 9 | 10* | 11 | 12 |
|---|---|---|---|---|---|---|
| Catalyst | CA | CA | CA | CD | CD | CD |
| Catalyst Concentration in Reactor Feed (ppm of cobalt) | 1.4 | 5.0 | 10.0 | 1.4 | 5.0 | 10.0 |
| Cyclohexane Feed Rate (g/hr) | 2490 | 2500 | 2500 | 2500 | 2480 | 2490 |
| Residence Time in Reactor (min) | 8.5 | 8.5 | 8.5 | 8.5 | 8.5 | 8.5 |
| Cyclohexane Conversion (%) | 4.12 | 4.13 | 4.08 | 3.94 | 4.04 | 4.08 |
| Yield (%) | | | | | | |
| K | 20.9 | 21.3 | 21.1 | 23.9 | 24.5 | 23.7 |
| A | 35.6 | 39.3 | 40.5 | 38.5 | 40.5 | 40.7 |
| P | 15.1 | 11.6 | 10.4 | 7.8 | 5.0 | 5.4 |
| Total (K + A + P) | 71.6 | 72.2 | 72.0 | 70.2 | 70.0 | 69.8 |
| Productivity of KAP (g/hr) | 89.9 | 90.4 | 88.9 | 83.3 | 83.9 | 84.9 |

*The results given for Runs 7 and 10 are the results given for Runs 1 and 4, respectively, and are included for comparison.

TABLE III

| Run No. | 13 | 14* | 15* | 16* |
|---|---|---|---|---|
| Catalyst | CA | CD | CE | — |
| Catalyst Concentration in Reactor Feed (ppm | | | | |

TABLE III-continued

| Run No. | 13 | 14* | 15* | 16* |
|---|---|---|---|---|
| of cobalt) | 1.4 | 1.4 | 1.4 | 0 |
| Cyclohexane Feed Rate (g/hr) | 4500 | 4490 | 4540 | 4490 |
| Residence Time in Reactor (min) | 4.0 | 4.0 | 4.0 | 4.0 |
| Cyclohexane Conversion (%) | 2.39 | 2.42 | 2.25 | 2.30 |
| Yield (%) | | | | |
| K | 13.9 | 17.8 | 15.8 | 14.4 |
| A | 31.9 | 38.8 | 34.0 | 30.9 |
| P | 28.6 | 17.0 | 23.3 | 28.5 |
| Total (K + A + P) | 74.4 | 73.6 | 73.1 | 73.8 |
| Productivity of KAP (g/hr) | 100.6 | 98.1 | 93.1 | 96.2 |

*Runs 14–16 are comparative runs.

TABLE IV

| Run No. | 17 | 18 | 19 | 20** |
|---|---|---|---|---|
| Catalyst* | CA | CF | CG | CD |
| Catalyst Concentration in Reactor Feed (ppm of cobalt) | 1.4 | 1.4 | 1.4 | 1.4 |
| Cyclohexane Feed Rate (g/hr) | 2490 | 2500 | 2505 | 2505 |
| Residence Time in Reactor (min) | 8.5 | 8.5 | 8.5 | 8.5 |
| Productivity of KAP (g/hr) | 91.6 | 87.5 | 91.0 | 85.6 |

*CF = cobalt bis(2-ethylhexanoate) in combination with pyridine at a molar ratio of pyridine:cobalt of 4:1
CG = cobalt bis[di(2-ethylhexyl)phosphate] in combination with 4-cyanopyridine at a molar ratio of 4-cyanopyridine:cobalt of 4:1
**Comparative run.

TABLE V

| Phosphate Ester | N-heterocyclic Compound | Solubility of Cobalt Phosphate Ester/N-heterocyclic Compound |
|---|---|---|
| Diethylphosphate | Pyridine | No* |
| Diphenylphosphate | Pyridine | No* |
| Phenylphosphate (1:1 diester/monoester, molar basis) | Pyridine | No* |
| Diisoamylphosphate | Pyridine | No |
| Diamylphosphate (mixed isomers) | Pyridine | No |
| Dibutylphosphate | Pyridine | No |
| Di(n-octadecyl) phosphate | Pyridine | No |
| 2-ethylhexylphosphate (1:1 diester/monoester, molar basis) | Pyridine | No |
| Di(2-ethylhexyl) phosphate | Pyridine | Yes |
| Di(2-ethylhexyl) phosphate | 4-Cyanopyridine | Yes |
| Di(2-ethylhexyl) phosphate | 4-Methylpyridine | Yes |
| Di(2-ethylhexyl) phosphate | Dipyridyl | Yes |
| Di(2-ethylhexyl) phosphate | Pyrazine | Yes |
| Di(2-ethylhexyl) phosphate | 2-Methoxypyridine | Yes |
| Di(2-ethylhexyl) phosphate | 4-Aminopyridine | No |
| Di(2-ethylhexyl) phosphate | 4-Hydroxypyridine | No |
| Di(2-ethylhexyl) phosphate | Nicotinic Acid | No |
| Di(2-ethylhexyl) phosphate | 4-Nitropyridine | No |
| Di(2-ethylhexyl) phosphate | Isonicotinamide | No |

*The cobalt phosphate ester was also not soluble in cyclohexane.

TABLE VI

| Run* | 21** | 22 | 23 |
|---|---|---|---|
| Catalyst | CD | CA | CA |
| Yield (%) | | | |
| K | 23.7 | 21.5 | 21.0 |
| A | 43.9 | 43.6 | 43.9 |
| P | 1.4 | 8.8 | 9.6 |
| Total (K + A + P) | 69.0 | 73.9 | 74.5 |

*Samples for each run were taken over a period of about 24 hours and the results were averaged.
**Comparative run.

EXAMPLE VII

In order to illustrate the solubility of cobalt bis[di(2-ethylhexyl)phosphate] and cobalt bis(2-ethylhexanoate) in hydrocarbon solvents in the presence and absence of pyridine, admixtures of hydrocarbon and cobalt compound in ratios, on a weight basis, of 90:10, 50:50 and 10:90 were prepared. Pyridine, if present, was used in an amount of 4 moles of pyridine per mole of cobalt compound. The results obtained are given in Table VI.

In related experiments, anhydrous cobalt (II) acetate was admixed with cyclohexane and with cyclododecane so that excess cobalt acetate was present. After allowing the excess cobalt acetate to settle, the cobalt metal concentration was determined using a flame ionization spectrometer. It was found that in cyclohexane, the cobalt metal concentration was 4.5 ppm and 6.5 ppm at 25° C. and 65° C., respectively; while in cyclododecane at 65° C., the concentration was 45 ppm. In the presence of pyridine (4 moles pyridine per mole of cobalt acetate admixed with hydrocarbon), the cobalt metal concentration increased to 70 and 273 ppm in cyclohexane at 25° C. and 65° C., respectively, but decreased to 22 ppm in cyclododecane at 65° C. Thus, in the context of the present invention, cobalt (II) acetate is not soluble in hydrocarbon solvents.

TABLE VII

| Run No. | Compound | Pyridine Added | Temperature (°C.) | Soluble at Ratio of 90:10 | 50:50 | 10:90 | Cobalt Concentration (%) |
|---|---|---|---|---|---|---|---|
| (A) | Solvent = cyclohexane | | | | | | |
| 21a | CC | No | 25 | Yes | Yes | No | 3.8 |
| 21b | CC | Yes | 25 | Yes | Yes | Yes | 3.2 |
| 22a | CD | No | 25 | Yes | Yes | Yes | 6.0 |
| 22b | CD | Yes | 25 | Yes | Yes | Yes | 4.5 |
| 23a | CC | No | 25 | Yes | Yes | No | 3.8 |
| 23b | CC | Yes** | 25 | *** | No | — | 2.7 |
| 23c | CC | Yes** | 65 | Yes | Yes | No | 2.7 |
| (B) | Solvent = cyclododecane (m.p.-61–63° C.) | | | | | | |
| 24a | CC | No | 65 | Yes | Yes | No | 3.8 |
| 24b | CC | Yes | 65 | Yes | Yes | Yes | 3.2 |
| 25a | CD | No | 65 | Yes | Yes | Yes | 5.9 |
| 25b | CD | Yes | 65 | Yes | Yes | Yes | 4.4 |

CC = cobalt bis[di(2-ethylhexyl)phosphate]
CD = cobalt bis(2-ethylhexanoate)
*cobalt metal concentration in 50:50 hydrocarbon/cobalt compound admixture.
**4-cyanopyridine used instead of pyridine.
***approximately 30% of cobalt compound dissolved.
N.B. soluble = completely soluble on visual inspection.

I claim:

1. A process for the catalytic oxidation of a liquid cycloparaffin to partial oxidation products thereof which comprises introducing a molecular oxygen-containing gas into a cycloparaffin of from 5 to 12 carbon atoms at elevated pressure and at a temperature of from 130° to 180° C. and in the presence of an oxidation catalyst comprising cobalt bis[di(2-ethylhexyl)phosphate] in combination with pyridine, said oxidation catalyst being capable of forming a concentrate in the cycloparaffin, having a cobalt concentration of at least 0.1%.

2. A process for the catalytic oxidation of a liquid cycloparaffin to partial oxidation products thereof which comprises introducing a molecular oxygen-containing gas into a cycloparaffin of from 5 to 12 carbon atoms at elevated pressure and at a temperature of from 130° to 180° C. and in the presence of an oxidation catalyst comprising a heavy metal compound in combination with an N-heterocyclic compound, said heavy metal compound being selected from cobalt bis(2-ethylhexanoate) and cobalt bis[di(2-ethylhexyl)phosphate] and mixtures thereof, said N-heterocyclic compound being selected from pyridine and 4-cyanopyridine, and said oxidation catalyst being capable of forming a concentrate in the cycloparaffin, having a cobalt concentration of at least 0.1%.

3. A process according to claim 1 or claim 2 in which the cycloparaffin is cyclohexane.

4. A process according to claim 1 or claim 2 in which the cycloparaffin is cyclododecane.

* * * * *